United States Patent [19]

Leavitt

[11] Patent Number: 5,681,477
[45] Date of Patent: Oct. 28, 1997

[54] THERMALLY-DRIVEN ION-EXCHANGE PROCESS FOR LITHIUM RECOVERY

[75] Inventor: Frederick Wells Leavitt, Amherst, N.Y.

[73] Assignee: Praxair Technology, Inc., Danbury, Conn.

[21] Appl. No.: 547,749

[22] Filed: Oct. 25, 1995

[51] Int. Cl.$^6$ ................................................. C02F 1/42
[52] U.S. Cl. ................ 210/672; 210/673; 210/677; 210/678; 210/681; 210/687; 423/179.5; 423/181
[58] Field of Search ................ 210/677, 672, 210/673, 678, 687, 686, 681; 423/179.5, 181

[56] References Cited

U.S. PATENT DOCUMENTS

| | | | |
|---|---|---|---|
| 2,631,727 | 3/1953 | Cichelli | 210/672 |
| 2,980,497 | 4/1961 | Goodenough et al. | 423/181 |
| 2,980,498 | 4/1961 | Wheaton et al. | 423/181 |
| 2,980,499 | 4/1961 | Goodenough et al. | 423/181 |
| 3,033,641 | 5/1962 | Thomas | 210/681 |
| 3,295,920 | 1/1967 | Goodenough et al. | 423/181 |
| 3,542,525 | 11/1970 | Pigford et al. | 210/672 |
| 3,957,698 | 5/1976 | Hatch | 260/2.1 R |
| 4,031,155 | 6/1977 | Healy et al. | 210/672 |
| 4,031,156 | 6/1977 | Geissler et al. | 210/672 |
| 4,116,856 | 9/1978 | Lee et al. | 252/184 |
| 4,139,499 | 2/1979 | Wade et al. | 521/32 |
| 4,159,311 | 6/1979 | Lee et al. | 423/179.5 |
| 4,184,948 | 1/1980 | Dabby et al. | 210/673 |
| 4,221,767 | 9/1980 | Lee et al. | 423/179.5 |
| 4,229,545 | 10/1980 | Eppinger et al. | 521/38 |
| 4,291,001 | 9/1981 | Repsher et al. | 423/179.5 |
| 4,293,423 | 10/1981 | Kosaka et al. | 210/676 |
| 4,324,564 | 4/1982 | Oliker | 95/129 |
| 4,376,100 | 3/1983 | Lee et al. | 423/179.5 |
| 4,404,118 | 9/1983 | Herskovits | 210/672 |
| 4,447,329 | 5/1984 | Broughton | 210/677 |
| 4,523,998 | 6/1985 | Kim | 210/638 |
| 4,540,509 | 9/1985 | Burba, III | 423/179.5 |
| 4,874,524 | 10/1989 | Liapis et al. | 210/672 |
| 5,032,156 | 7/1991 | Luder et al. | 55/269 |
| 5,094,755 | 3/1992 | Knaebel | 210/677 |
| 5,176,885 | 1/1993 | Impink, Jr. et al. | 423/6 |
| 5,389,349 | 2/1995 | Bauman et al. | 423/179.5 |
| 5,451,383 | 9/1995 | Leavitt | 423/179.5 |
| 5,464,467 | 11/1995 | Fitch et al. | 95/98 |
| 5,599,516 | 2/1997 | Bauman et al. | 423/179.5 |

*Primary Examiner*—Cynthia L. Nessler
*Attorney, Agent, or Firm*—Robert J. Follett

[57] ABSTRACT

Ions (e.g. lithium) can be removed or recovered from brines containing those ions and optionally one or more other ions (e.g. other alkali metal ions) by the use of a temperature-swing, ion-exchange process employing an ion-exchange material. The process depends on a change in the selectivity coefficient of an ion exchange material for the ions desired to be recovered with a change in temperature, resulting in desirable ions being relatively selectively released at one temperature and undesirable ions being relatively selectively released at another temperature. The process of the invention can be used to effect the separation of any ion (or set of ions) from another ion or from a set of ions wherein the selectivity coefficient for one ion (or set of ions) has a substantial temperature dependence, compared to that for the other ion (or set of ions).

17 Claims, 7 Drawing Sheets

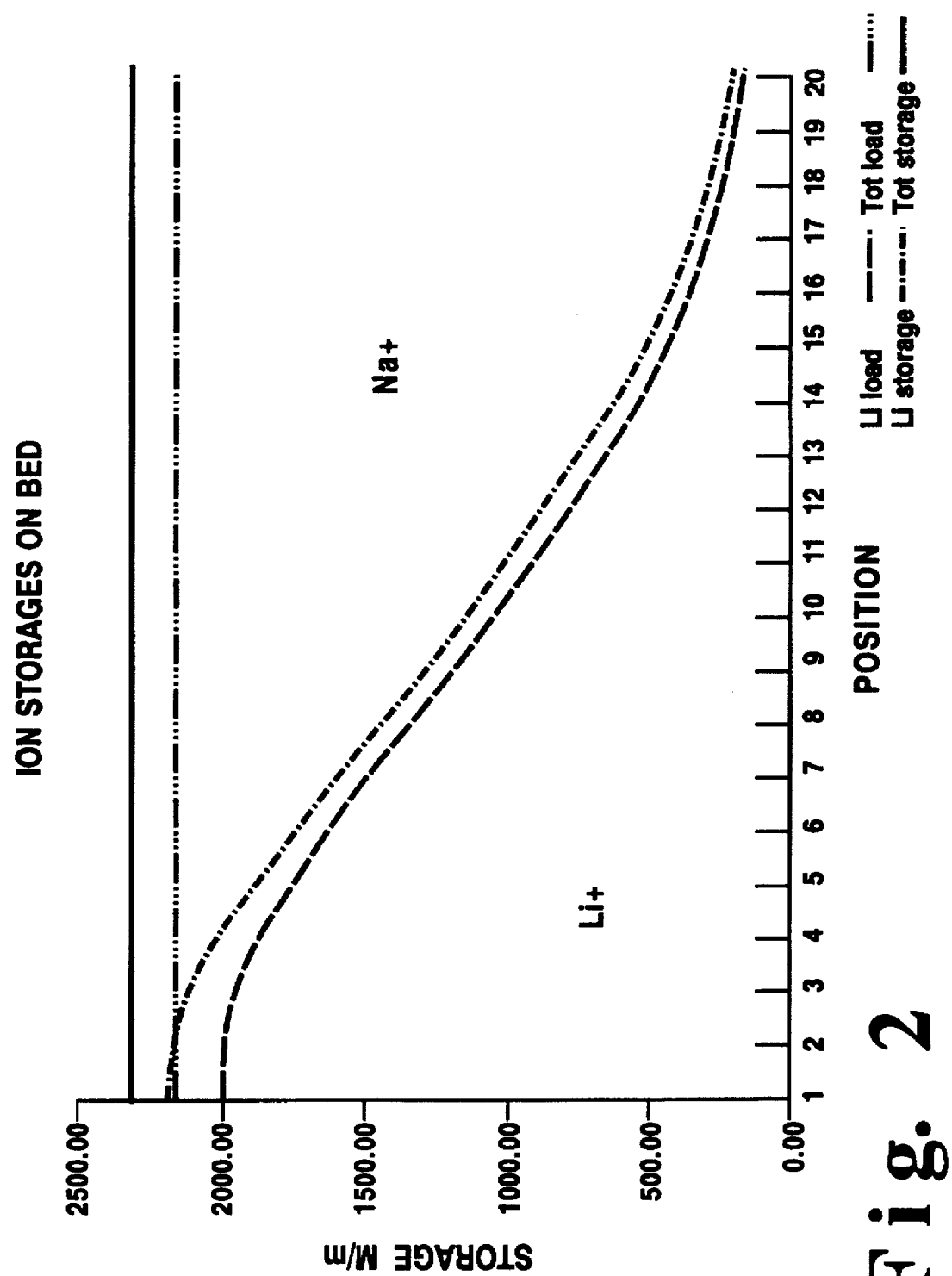

THERMALLY-DRIVEN ION-EXCHANGE PROCESS FOR LITHIUM RECOVERY

BACKGROUND OF THE INVENTION

1. Field of the Invention

The present invention relates to processes, or methods, for recovering lithium ions from lithium-containing aqueous solutions that also contain other alkali metal or alkaline-earth metal ions. More generally, the present invention relates to methods for separating one set of one or more ions from another set of one or more ions in situations wherein the selectivity of an ion-exchange adsorbent for the ion set sought to be separated has a substantial temperature dependence.

Zeolite adsorbents ("molecular sieves") are used commercially as adsorbents in "pressure-swing" processes for separating and purifying gases. For the production of oxygen and/or nitrogen, it has been found that zeolites containing $Li^+$ ions (such as LiX or LiCaX zeolites) have particularly desirable properties. Lithium-containing zeolites ($Li^+$ zeolites) are prepared from the corresponding $Na^+$ zeolites by ion exchange. Typically, a concentrated aqueous solution of $Li^+Cl^-$ is passed through a column containing the $Na^+$ zeolite. The $Na^+$ ions in the zeolite are displaced by the $Li^+$ ions to produce the desired $Li^+$ zeolite. Since zeolites generally have a greater affinity for the $Na^+$ ion than for the $Li^+$ ion, a considerable quantity of concentrated $Li^+Cl^-$ solution is required and the spent liquor ("brine") contains a high concentration of both $Na^+$ and $Li^+$ ions. The contained lithium is valuable too, therefore its recovery from the spent liquor is highly desirable.

Additionally, after conversion, the Li-exchanged zeolite must be washed and dried. The spent wash water also contains $Li^+$ ions. In current processes, these are not recovered but are lost in the discharged waste water. Quantities of lithium are also lost in Li-exchanged zeolite that does not meet specifications. This lithium also can be released into solution (e.g. by displacement with $Na^+$) but in practice this is not done principally because of the cost involved.

According to current practice, only concentrated brines (i.e. brines containing at least 1.8 ion-equivalents/liter) are processed for lithium recovery. Under current practice, the brine is subjected to evaporative concentration and fractional crystallization to remove by precipitation most of the NaCl, leaving a relatively uncontaminated $Li^+Cl^-$ solution which can be reused in the ion-exchange process. Dilute $Li^+$-containing solutions (typically, those containing less than about 1.3 ion-equivalents/liter) would require large amounts of thermal energy to treat in this manner and are discharged as waste. (Because the current practice involves evaporation and fractional crystallization, the quantity of the valuable ions in the solution is the principal relevant factor to the decision to proceed with lithium recovery.) Unlike NaCl, which is abundant and inexpensive, LiCl is rare and costly. The total lithium lost to waste thus adds appreciably to the overall cost of the zeolite manufacturing process.

There is thus a need for improved processes for recovering $Li^+$-ions from both concentrated and dilute brines that contain $Li^+$ and $Na^+$ alone or in combination with other alkali and alkaline earth cations, and are generated in zeolite (or other ion-exchanged media) manufacture. There is also a need for processes for recovering valuable $Li^+$ from aqueous mixtures containing lithium and other cations, such as fluids of spent lithium batteries. A need also exists for a method of recovering valuable ions from solutions and for producing concentrated solutions containing valuable ions without employing evaporation or fractional crystallization.

Temperature variations to cause adsorption or desorption of ions from ion-exchange materials have been employed in the past in various other contexts. For example:

1) U.S. Pat. No. 5,176,885 by Albert J. Impink and Joseph A. Battaglia, assigned to Westinghouse Electric Corp., entitled *Isotope Separation of Weak Acid Forming Elements by Utilization of Thermal Regeneration of Ion Exchange Resin*. The process described in this patent is directed to the separation and concentration of boron isotopes (Boron-10) in acidic solutions, and involves circulating a solution at a high temperature through one ion-exchanger and then cooling down the solution and passing it through another ion-exchanger. The abstract states that "the separation is accomplished by shifting the equilibrium constants for adsorption and desorption by temperature variations of the acidic solution". However, the enrichment of the solution in Boron-10 is very gradual and the process takes several months to achieve significant enrichment. Moreover, there is no production of two different streams with significant variation in composition, and the process appears to depend mainly on differential transfer rates rather than differences in equilibrium.

2) U.S. Pat. No. 4,523,998 by Bang M. Kim, assigned to General Electric Co., entitled *Continuous Ion Exchange Process Using Thermally Regenerated Liquid Ion Exchangers*. This patent describes the use of liquid ion-exchange materials for removal of mineral ion species from aqueous streams. The concentration step is carried out by introducing the solution to be stripped of a mineral ion species in a first vessel which is kept at a low temperature and adsorbing the ion onto an ion-exchange material. The mineral species is then released by introducing the ion exchange material into a second vessel kept at a high temperature (where the ion-exchange capacity is lower) causing the mineral species to be released into the aqueous phase. This process results in removal of mineral species from a liquid but does not separate ionic species from each other. Moreover, it requires liquid ion exchange materials (which in turn require a large fluid-fluid interface) and a large shift in equilibrium between the two temperatures in order to reduce the quantity of hot water required to carry off the undesirable minerals.

3) U.S. Pat. No. 4,293,423 by Kenji Kosaka, Takeshi Iwatsuka, Ikuo Shindo and Akira Hotogi, assigned to Rohm and Haas Co., entitled *Process and Apparatus for Ion Exchange by Use of Thermally Regenerable Resin*. Ion-exchange treatment, such as desalination, is achieved by utilizing a column packed with a heterogeneous thermally regenerable ion exchange resin in a bed divided into different zones. The resin removes ions in one zone. It is then transferred to a different zone where it is heated to release the ions. Again, there is no separation of one ionic species from another.

OBJECTS OF THE INVENTION

It is accordingly an object of the invention to provide a simpler, less costly and more energy-efficient process for recovering desirable ions (e.g. lithium ions) from concentrated or dilute solutions containing such ions alone or together with other undesirable ionic species.

It is another object of the invention to provide a method for upgrading the quality of ion-containing (e.g. lithium-containing) solutions by removing contaminant ions (such as sodium and calcium) and/or by enriching the ion content (e.g. increasing the lithium content) of such solutions.

It is a further object of the present invention to provide a method for separating a first set of one or more desirable ions from a solution also containing a second set of one or more different (undesirable) ions, in which the selectivity coefficient K of an ion-exchange material for the first (or the second) set of ions is temperature dependent, such that the selectivity coefficient K for one set of ions is higher (even very slightly higher) at a first temperature than at a second temperature different from the first temperature.

These and other objects of the present invention will be apparent to those skilled in the art in light of the present specification, claims and drawings.

BRIEF DESCRIPTION OF THE DRAWINGS

FIG. 2 is a graph of the concentration gradient of $Li^+$ storage and loading (in ion-equivalents/unit volume of the ion-exchange bed) as a function of position (percent length) in the direction of liquid flow within an ion-exchange bed at a constant total ($Li^+$ and $Na^+$) ion storage during a process step in which $Li^+$ is taken up by the bed.

SUMMARY OF THE INVENTION

Figure 1:
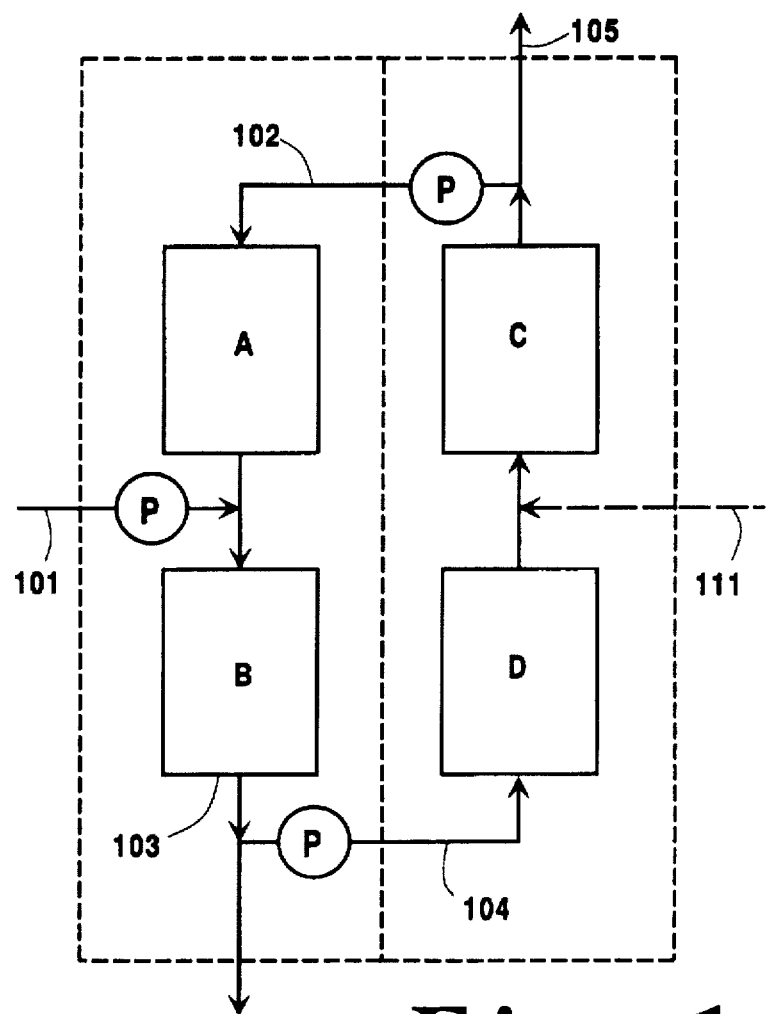
FIG. 1 is a process schematic of a duplex embodiment of an ion-exchange process according to the invention in which two trains of two ion-exchange beds each are employed for separation of $Li^+$ from a solution also containing $Na^+$.

Ions (e.g. lithium) can be removed or recovered from brines containing these ions and optionally one or more other ions (e.g. other alkali metal ions) by the use of a temperature-swing, ion-exchange process employing an ion-exchange material. The process depends on a change in the selectivity coefficient of an ion exchange material for the ions desired to be recovered with a change in temperature, resulting in desirable ions being relatively selectively released at one temperature and undesirable ions being relatively selectively released at another temperature. The process of the invention can be used to effect the separation of any ion (or set of ions) from another ion or from a set of ions wherein the selectivity coefficient for one ion (or set of ions) has a substantial temperature dependence (or strong temperature sensitivity), compared to that for the other ion (or set of ions). In another aspect, the invention is directed to apparatus for carrying out the process.

DETAILED DESCRIPTION OF THE INVENTION

This invention comprises a thermally-driven ion-exchange process that can recover Li+ from concentrated or dilute brines in a single processing unit. The process of the invention is more energy efficient and simpler than evaporation and fractional crystallization, and permits e.g. lithium-containing solutions to become enriched in lithium and/or (if applicable) impoverished in undesirable ions.

The use of the ion-exchange process of the invention also permits cost- and energy-efficient recovery of lithium that is normally discarded in the manufacture of specialty zeolite adsorbents, resulting in appreciable savings in overall manufacturing costs. Additionally, the process of this invention permits the use in zeolite manufacture of lower-cost, lower-purity lithium salts as starting materials, since contaminant ions can be removed by the process of the invention, before solutions of these lithium-containing materials are used in such manufacture.

As the terms are used herein:

(a) "concentrated" is a brine having a total ion concentration of at least about 0.5 ion-equivalents per liter;

(b) "dilute" is a brine having a total concentration of at most about 0.5 ion-equivalents per liter;

(c) "DI-rich" or "DI-enriched" is a solution (brine) having a desirable ion (DI) concentration (in equivalent percent of the total cations or anions) higher than the feed solution, preferably higher than 50 and most preferably higher than 90 equivalent percent of total cations or anions; conversely, "DI-poor" or "DI-impoverished" is a solution having a desirable ion concentration lower than the feed solution; "UI-rich" and "UI-poor" have analogous meanings for solutions containing undesirable ions (UI);

(d) the selectivity of an ion-exchange material for a particular ion has a "strong temperature dependence" when the selectivity for that ion changes by a factor of at least about 1.4 when the temperature changes from ambient to near the boiling point of water;

(e) "loading" of an ion is the number of molar equivalents of that ion actually "adsorbed" (held in ion exchange) in a cubic meter of an ion-exchange material;

(f) "storage" of an ion is the sum of loading plus the number of molar equivalents of that ion in solution contained within a cubic meter of ion-exchange material, i.e. the solution contained in the crystal structure, the pores and in the inter-particulate space of the material;

(g) "zone" refers to the environment in which a portion of the process of the invention is performed; thus, a "cold zone" refers to an environment maintained at a low operating temperature in which a portion of the process is performed; a "zone" can be hot or cold at different phases during a process cycle. In other words, a "cold zone" is a zone that is in a "cold phase";

(h) "bed" is a batch of ion exchange material typically contained in one vessel (which may be a column);

(i) "train" is a set of two or more beds of ion-exchange material connected in-series within the same zone.

Although the following invention is described mostly by reference to zeolites, to recover lithium from solutions containing lithium alone or in combination with other alkali or alkali metal ions, it also has applicability to a wide variety of ion-exchange media including ion-exchange resins, and to a variety of cations and anions.

It should be noted that the designations herein "desirable ion" and "undesirable ion" are used for convenience only, as both the cold-released and the hot-released ions may be valuable and their recovery desirable. Similarly, the designation "top" and "bottom", applied to various parts of the process and apparatus, are also employed only for convenience, as the collection points for each ion or ion mixture may be reversed. Furthermore, although it is preferred to run the process in a vertical arrangement, it could also be run horizontally. If the process is run in a vertical arrangement, it is preferred to collect the lighter ion(s) (e.g. $Li^+$) at the top and the heavier ion(s) (e.g. $Na^+$) at the bottom.

Any feature described with respect to one embodiment should be deemed to have been described with respect to other embodiments of the invention if desired.

The invention may be used to recover lithium cations for the production of lithium-exchanged zeolites and for all other processes employing ionic solutions that are potentially enrichable in valuable cations the selectivity of which for a particular solid adsorbent varies with temperature as provided above (and is different from the selectivity of undesirable ions contained in the same solution). Ion-exchanged media that can be used to enrich such solutions include, without limitation, zeolites with exchangeable cations, cation-exchange resins, anion-exchange resins and fabrics or structures with exchangeable cations or anions. Ion-exchange media in each category are commercially available.

In a preferred embodiment, the invention comprises a "temperature-swing, ion-exchange process" to separate $Li^+$ ions from $Na^+$ and $K^+$ ions (and, in addition or alternatively, also $Ca^{++}$ and heavier alkaline earth ions) from process brine streams. The process depends on the fact that the ion-selectivity of zeolite X (or another suitable ion-exchange material) exhibits a strong temperature sensitivity, at least for $Li^+$ ions, relative to other alkaline and alkaline earth ions. This temperature sensitivity permits the construction of a cyclic, reversible process that in turn permits the nearly complete separation of $Li^+$ ions from the $Na^+$ ions (and other alkali and alkaline earth ions). The extent of the separation (in terms of recovery and purity) can be controlled by the amount of reflux employed in the process (which in turn determines the size or capacity of the system).

In the presence of $Li^+$—$Na^+$—brine, the total storage of ions in the brine and on a zeolite bed is effectively constant and independent of the temperature. The ion-selectivity of the zeolite is, however, temperature dependent. The zeolite favors $Na^+$ over $Li^+$ at all temperatures, but the selectivity of the zeolite for sodium over lithium is greater at low temperatures than at high temperatures. When a zeolite bed, initially in equilibrium with a brine containing both ions, is heated, there is an exchange of $Na^+$ ions from the zeolite to the brine, while $Li^+$ ions move from the brine to the zeolite. The reverse happens when the bed is cooled. $Li^+$ moves from the zeolite to the brine, being replaced by $Na^+$ ions. This exchange of ions from brine to zeolite, and vice versa, is the basis of the separation employed in the invention.

Since the ion-selectivity of the zeolite strongly favors $Na^+$ ions over $Li^+$ ions, only a modest amount of $Li^+$ can be concentrated in the brine by merely lowering the bed temperature. This effect can be amplified, however, by deploying the zeolite in beds or in "trains" of several beds and alternating the direction of flow of the brines and the temperature of one or more beds. The result is a "temperature-swing ion-exchange" process, analogous to the "temperature-swing" and "pressure-swing" adsorption processes that are used for the separation of gasses. In operation, the ion-exchange bed will develop an ion-concentration gradient wherein the adsorbed $Li^+$ is concentrated at one end of the bed and $Na^+$ is concentrated at the other end. An example of such a concentration gradient is depicted in FIG. 2. In FIG. 2, the abscissa represents the position in an ion-exchange medium bed in the direction of liquid (brine) flow during a step in which lithium is being taken up by the bed. In the example, the total ion concentration with feed brine is equal to that of the brine initially in the bed. The feed brine is richer in lithium than the brine initially in the bed. The total storage for both lithium and sodium ions (ions in liquid plus ions held on the ion-exchange medium) in thousands of moles preferably remains constant, as shown in FIG. 2. However, the feed brine being rich in lithium, the adsorbed lithium is higher at the end of the bed near the feed and the adsorbed sodium is higher at the end of the bed remote from the feed entry point.

In a particularly preferred embodiment, the process of the invention comprises a "duplex, temperature-swing, ion-exchange process" as depicted in FIG. 1. Four ion-exchange beds (A through D) in two in-series pairs (A–B and C–D), loaded with zeolite-X ion-exchange material, are depicted in FIG. 1, representing a particularly preferred embodiment, but the process could be conducted with only one pair of beds (one kept hot and one kept cold during each part of a two-part cycle) or even a single bed as in FIG. 9 with appropriate surge tanks (901–903) to store feed brine while the temperature is being changed, or to store product brine which can then be used as reflux (the single bed is alternatively heated and cooled).

In FIG. 1, two of the beds (C and D during the first phase of the temperature-swing cycle) are maintained at a relatively low average temperature, i.e. constitute the cold zone, while the other two beds (A and B during the same phase) are maintained at a relatively high average temperature, i.e. constitute the hot zone.

In the process depicted in FIG. 1, the zone containing the gradient of the type depicted in FIG. 2 is divided into two beds, A and B, so that the fluid composition at the junction between the two beds is relatively close to that of the feed brine, 101. The feed can be introduced either in the hot zone, 101, or the cold zone, 111, the choice depending primarily on the temperature of the feed stream. If the feed is at a temperature close to that of the hot zone, then that zone is preferred for feed introduction. Of course, it is possible to change the temperature of the feed as well as its composition if desired and it is further preferred to alternate the feed introduction point, when the cold and hot zone are interchanged. Furthermore, the feed may be introduced continuously (during both the hot and the cold phases) or intermittently (during at least a portion of a phase), the choice being of the process operator and depending on product specifications and other product control parameters as is well-appreciated in the field of the invention.

As shown in FIG. 1, a $Li^+$-rich reflux, or recycle stream, 102, is injected into the top of bed A. The lithium ion-gradient moves downward through beds A and B and $Na^+$-rich brine emerges from the bottom 103 of bed B. Simultaneously, a $Na^+$-rich reflux (a portion of the $Na^+$-rich bottom product brine) 104, preferably after cooling (not shown), is injected into the bottom of bed D.

In the cold zone, the Li$^+$ concentration gradient moves upward in beds D and C and Li$^+$-rich brine emerges from the top of bed C. When the purity of the top product 105 begins to degrade, the flows must be stopped and the temperature is "swung" to the second phase of the cycle. During the second phase, beds A and B are cooled (cold zone) and beds C and D are heated (hot zone) and the directions of the flows are reversed. (This can be visualized by mentally interchanging beds A and C and beds B and D in FIG. 1.) Depending on the reflux ratio, the purities of the Li$^+$-rich and Na$^+$-rich products can be controlled to suit the specifications dictated by the problem. For example, if it is desired to increase purity of the lithium-rich product, the reflux ratio can be increased, and/or the size of beds A and C can be increased, and/or the particle size of the ion-exchange material in beds A and C can be decreased (this both increases surface area and decreases diffusion path length; both changes favor higher purity). If on the other hand it is desired to increase recovery of the lithium-rich product, the reflux ratio can be increased, and/or the size of beds B and D can be increased, and/or the particle size in beds B and D can be increased.

It will be appreciated that the operating temperature (more correctly the average operating temperature) of the "hot" (or of the "cold" zone) during the first half of the cycle need not be exactly duplicated during the second half of the cycle when the hot and cold zones are switched. It is sufficient that the average temperatures of the "hot" zones be substantially the same (i.e. differ by no more than about 10° C.). The same holds true for the "cold" zones.

Other parameters that need to be monitored are well-known to those skilled in the art and include: (a) flow rates below those causing fluidization and above those causing channelling; (b) suitably large temperature differences between the "cold" and the "hot" zone (to take advantage of the temperature sensitivity of the selectivity of the ion-exchange material for the desired ion); (c) choice of the ion-exchange material (to display a temperature dependent selectivity for the desired ion that permits its separation, and to withstand operating temperatures); (d) maintenance of a high average temperature in the "hot" zone and a low average temperature in the "cold" zone; and (e) prompt shut off of flows when the purity and/or recovery of the desired ions in the product stream declines.

The process of the present invention can optionally be carried out with trains comprising more than two beds. In FIG. 1 there are two trains of two beds each (A & B, and C & D).

Figure 9:
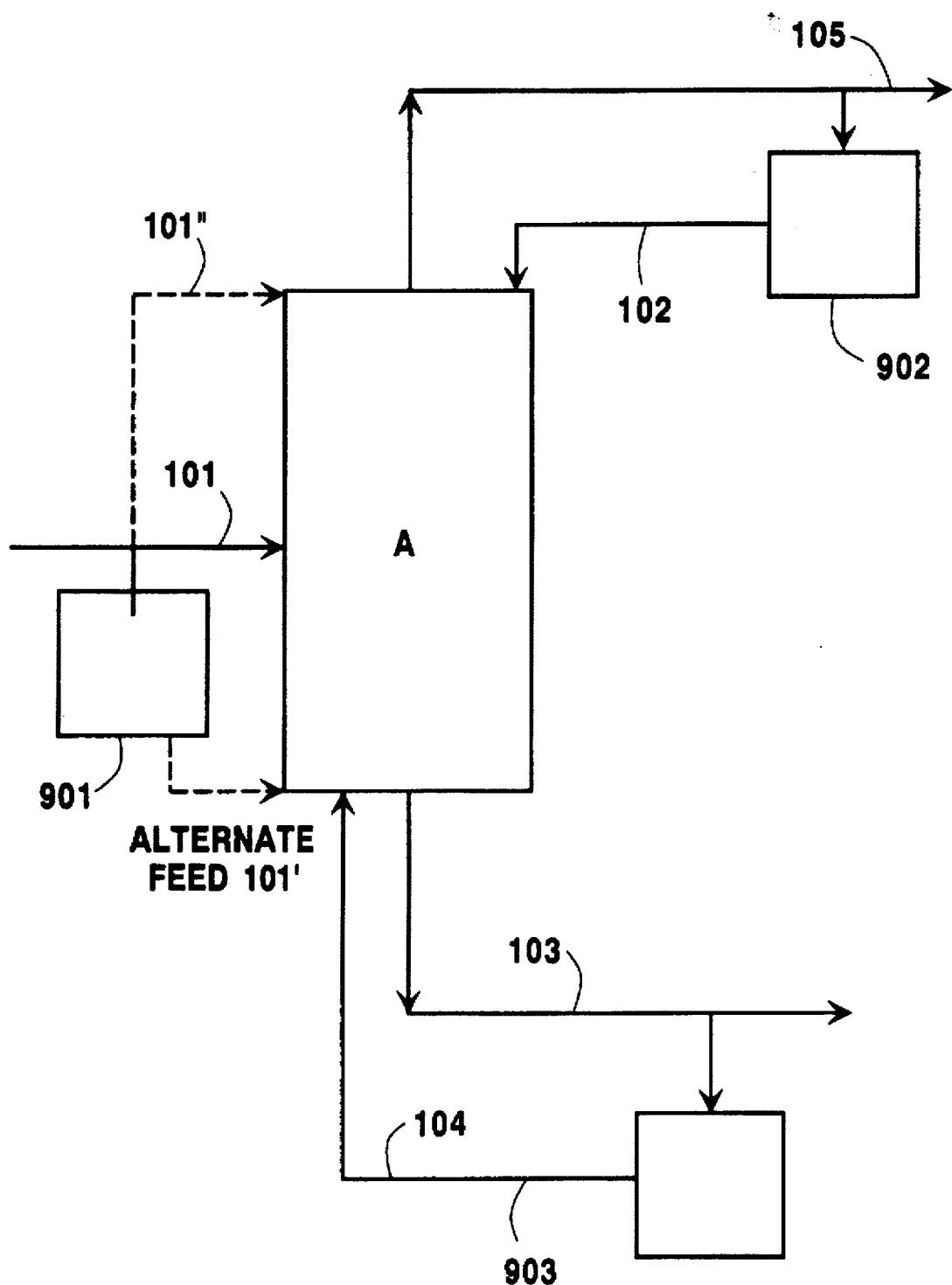
FIG. 9 is a process schematic of a single zone in a duplex (single-bed but intermediate feed) separation process according to the invention.

Feed brine is preferably added to a point part-way through a train (if the train has only one bed, the feed is preferably introduced part-way through the bed which then functions as two beds, such as A and B in FIG. 1; see FIG. 9) it may be added in one or both trains only during a cold phase of the cycle; or only during a hot phase of the cycle; or during both a cold phase and a hot phase. If purity of the hot-released ion is not important, then the feed may be introduced at a point in a train that is as much removed as possible from the point of collection of the product enriched in cold-released ion. If purity of the cold-released ion is not important, then the feed may be introduced at a point in a train that is as much removed as possible from the point of collection of the product enriched in hot-released ion. Feed introduction may be subject to further optimization as is well-known in the art.

During a cold phase for one of the zones, a product enriched in cold-released ions (e.g. lithium) is produced; part of this product is collected as the end product and part is used for reflux during part or all of a hot phase of one (or more) of the other zones (or in the same zone when the cycle switches to hot).

During a hot phase for one of the zones, a product enriched in hot-released ions (e.g. sodium) is produced; part of this product is collected as the end product and part is used as a reflux during part or all of a cold phase of one (or more) other zones (or in the same zone when its cycle switches to cold).

The reflux ratio of either the product enriched in hot-released ion or the product enriched in cold-released ion can be adjusted to advantage as described above. (It will be understood that the reflux ratios are interdependent, as is well-known.)

For cation separation, generally, suitable ion-exchange materials include without limitation the aforedescribed zeolites X, zeolites A, mordenite, clinoptilolite, erionite, etc., as well as various organic ion-exchange materials widely described in the literature as thermally regenerable or thermally reversible ion-exchange resins. Zeolites X are preferred; most preferred are X zeolites having a silica/alumina ratio of 2.0 to 3.0. Various zeolites have been described in the patent literature, e.g. U.S. Pat. Nos. 2,882,244; 3,140,932; 3,140,933; 4,859,217; 5,266,102; and 5,152,813, incorporated by reference in their entirety. For non-zeolite cations exchange materials, see, e.g. Perry's Chem. Eng. handbook, Fourth Edition, McGraw Hill Book Co., Chapter 16, incorporated by reference, especially Table 16-2. Preferred non zeolite cation exchange materials are various sulfonated polystyrene resins, such as Amberlite (Rohm & Haas) and DOWEX 50 (Dow Chemical Co.) which have quite elevated maximum operating temperatures. See, also e.g., U.S. Pat. Nos. 4,229,545 (Eppinger et al.); 4,184,948 (Dabby et al.); 4,139,449 (Wade et al.); and 3,957,698 (Hatel et al.) all incorporated by reference in their entirety.

For anion separation, generally, suitable ion-exchange materials include without limitation trimethyl benzyl ammonium type resin with polystyrene matrix, trimethylaminoethyl cellulose, aminoethyl cellulose, epoxy-polyamine, and other anion-exchange materials. See Perry, Ch. 16, supra., especially Table 16-3. Preferred are weakly basic aminopolystyrene resins such as AMBERLITE IR45 or IMAC19, both commercially available.

The choice of the ion-exchange material is dictated by its capacity to adsorb the ion of choice, and its possessing the requisite increase in selectivity for the ion of choice (relative to the other ions present) within the different operative temperature levels. This information is available for a variety of ion-exchange materials (e.g. in Breck, infra, for zeolites or in chemical Engineers' Handbook, John H. Perry, Fourth Edition, McGraw-Hill Book Company, Inc., New York, pp. 16-6 to 16-7 incorporated by reference in its entirety, for ion-exchange resins) or can be obtained from the manufacturer of an ion-exchange material).

Thus, a wide variety of ion-exchange materials can be used to effect ion separation according to the invention, provided that their selectivity for ions is temperature dependent and the temperature dependence varies even slightly between two ions to be separated.

Examples of the cations that can be separated include without limitation:

Li$^+$ from one or more other alkali metal cations
Na$^+$ from K$^+$
Rb$^+$ and/or Cs$^+$ from one or more alkali metal cations
Ba$^{++}$ and/or Sr$^{++}$ from Ca$^{++}$ and/or Mg$^{++}$
uranyl (uranium oxide cation) from other cations.

Examples of the anions that can be separated include without limitation:

F$^-$ from one or more of the other halide ions
I$^-$ from one or more of the other halide-ions It should be noted that use of the same ion-exchange material in all stages (i.e. beds and trains) of a process is preferred but not required. Of course, if more than one ion-exchange materials are used, this selectivity for a particular ion should have qualitatively the same relationship to temperature, i.e. all ion-exchange materials used should release the same ion(s) during the "cold" phase and should hold the remaining ion(s) during the "hot" phase.

The design for a process of separation of a given ion from a solution of ions according to the invention takes into account the following considerations:

A. Temperature Dependence of Ion Exchange

A bed of cation-exchange material can be brought into equilibrium with a brine containing various salts and their cations. For each pair of cations, V and W, there will be an equilibrium relation between the concentration ratio of V to W in the brine solution and the "loading" ratio of V to W in the ion-exchange material. The relationship will depend on brine composition, and the properties of the ion-exchange material.

Also, as is required for practice of the present invention, the equilibrium relationship between the ratio of V and W in the zeolite and in the solution will depend on the temperature. For some ion-exchange materials and cation pairs (exemplified above), the effect of temperature on the equilibrium relationship is pronounced, reflecting a strong net enthalpy of ion-exchange. An increase in temperature will then change the equilibrium relationship in the direction that encourages one of the cations to move from the brine into the ion-exchange material, replacing the other, so as to reduce the total enthalpy.

Information about the effect of temperature on ion-exchange equilibrium in zeolites has been given by Breck (D. W. Breck, *Zeolite Molecular Sieves*, Chapter 7, Wiley & Sons 1974) incorporated by reference in its entirety. Some values for the standard free energy and enthalpy for the exchange of $Na^+$ by other alkali and alkaline earth ions on zeolite X, taken from Breck, supra, Table 7.4, p 543, are given below:

TABLE 1

Cation Exchange in Zeolite X

| Exchange Reaction | Si/Al | Conc. | T (°C.) | $\Delta G^0$ (cal/g equiv) | $\Delta H^0$ (cal/g equiv) |
|---|---|---|---|---|---|
| $Na^+ \to Li^+$ | 1.21 | 0.1 m | 25 | 1350 | 1790 |
| $Na^+ \to K^+$ | 1.21 | 0.1 m | 25 | −190 | −1250 |
| $Na^+ \to Rb^+$ | 1.21 | 0.1 m | 25 | −1300 | −1500 |
| $Na^+ \to Cs^+$ | 1.21 | 0.1 m | 25 | −780 | −1660 |
| $Na^+ \to 1/2Ca^{++}$ | 1.26 | 0.1 m | 25 | −320 | 1200 |
| $Na^+ \to 1/2Sr^{++}$ | 1.26 | 0.1 m | 25 | −740 | 530 |
| $Na^+ \to 1/2Ba^{++}$ | 1.26 | 0.1 m | 25 | −1310 | −430 |

These values can be used to calculate the effect of temperature on the loading selectivity of the zeolite X for different ions. The loading selectivity coefficient K is thermodynamically related to the free energy $\Delta G^0$ of the ion-exchange process by the equation:

$$\ln K = -\frac{\Delta G^0}{RT} \quad (1)$$

For the exchange of univalent ions, K is identical with the separation factor. The variation of K with temperature T is determined from the enthalpy $\Delta H$ by the equation:

$$\frac{d\ln K}{dT} = \frac{\Delta H^0}{RT^2} \quad (2)$$

Using the values from the first row of Table 1 to calculate the loading K-values at 298 K (room temperature) and 370 K (near the boiling point of water) we obtain:

$$\text{at } T = 298.15\,K \quad K_{Na}^{Li} = 0.102 \quad K_{Li}^{Na} = 9.77 \quad (3)$$

$$\text{at } T = 370\,K \quad K_{Na}^{Li} = 0.184 \quad K_{Li}^{Na} = 5.43$$

As the selectivities show, the zeolite favors $Na^+$ over $Li^+$ at both temperatures, but changing the temperature from 298 K to 370 K decreases the selectivity for $Na^+$ by a factor of 1.8. Thus when the system is heated, $Li^+$ from the solution displaces some $Na^+$ on the zeolite. Conversely, upon cooling, $Na^+$ from the solution displaces $Li^+$ on the zeolite. The total ion storage (sum of the ions in solution and on the zeolite) remains constant if the heating and cooling is done without brine flow, but the partition of $Li^+$ and $Na^+$ between the zeolite and solution changes.

The data in Table 1 indicate that a thermal-swing process will easily effect a separation of $Li^+$ from $Na^+$, due to the large enthalpy difference. It is even easier to separate $Li^+$ from $K^+$ because the enthalpy difference of cation exchange is greater for this pair of ions. It would be more difficult to separate $Li^+$ from $Ca^{++}$ in a thermal-swing process because the enthalpy difference is smaller for this pair of ions than for $Na^+/Li^+$. $Li^+$ can nevertheless be separated from $Ca^{++}$ using, e.g., a larger reflux (and therefore a larger capacity system) than would be required to separate $Li^+$ from $Na^+$.

Similar shifts in the concentrations of other cation groups can be created with other cation-exchange materials by heating or cooling.

Shifts in the concentrations of anion groups could be created with anion-exchangers by heating or cooling in the same way. All that is needed is a set of ion-exchange equilibria that have the requisite temperature sensitivity, as explained above.

B. Binary Separation Ion-Exchange Systems

To make a clean separation (i.e. produce high purity products) of a pair of ions, a bed or a train of beds of ion-exchange material can be employed with reversing-flow brine streams. A relatively cool brine stream is forced through the bed in one direction (called "forward" for purposes of this discussion) and then a relatively hot brine stream is forced through the train in the opposite direction (called "backward" for purposes of this discussion). The train is continually cycled between the two temperature levels and with the two brine streams.

At any point in the train, the ion-exchange material must have a higher selectivity for one of the ions to be separated, e.g. ion V, at the higher temperature than at the lower temperature. The selectivity of the ion-exchange material for ion V may be less than unity or greater than unity so long as the selectivity is greater at the higher temperature than at the lower temperature. Under these conditions, the ion-exchange material at a point in the train will act to release ion V into the forward stream at the lower temperature (cold-released ion) and take it up from the backward stream at the higher temperature. Thus the ion-exchange material will work to remove ion V from the backward stream and "pump" it into the forward stream. The material will pump the other ion, ion W, in the reverse direction, abstracting ion W from the forward stream and releasing into the backward stream. If all points of the train do the same pumping, then the forward stream will be steadily enriched in ion V and depleted in ion W as it flows through the train. The backward stream will be steadily enriched in ion W and depleted in ion V as it flows through the train.

If more than two cations (or more than two anions) are involved, the ions can be separated into a cold-released ion (or set of ions) and a hot-released ion (or set of ions). The separation process is as for a single pair of ions, the purity of e.g. the cold-released product being the equivalent fraction of cold-released ions to the total amount of ions in the cold-released product streams. The separation process can be completed by feeding the mixture to be separated at a point in the train that is distant from both ends of the train. Then the flows in the train (which are reversed when the temperature of the zone containing the train is changed) will carry the ions (or ion groups) to opposite ends of the train. The forward flow will be steadily enriched in ion (or ion group) V as it moves through the train. If the exit of the forward flow from the train is far enough from the feed point, then the forward flow will be nearly pure in ion (or ion group) V at said exit. The backward flow will be steadily enriched in ion (or ion group) W as it moves through the train. If the exit of the backward flow from the train is far enough from the feed point, then the backward flow at its exit will be nearly pure in ion (or ion group) W. If high purity ion (or set of ions) W is not desired, then the part of the train from the feed point to the exit of the backward flow (e.g. number of beds, or size of beds or both) can be reduced in size or omitted. If high purity of ion (or group of ions) V is not desired, then the part of the train from the feed point to the exit of the forward flow can be reduced in size or omitted.

One important application of a multicomponent separation is the separation of lithium ions from a mixture of sodium and potassium ions. The preferred ion-exchange material is zeolite X for any bed or train. The cold-released product is enriched in lithium while the hot-released product is impoverished in lithium.

Cold-released ions have positive heat of ion exchange relative to hot-released ions. See, e.g. Table 1. Further information about ion-exchange selectivity and temperature effects is available in the literature. See, e.g. Helfferich, F. *Ion Exchange,* Chapter 5 McGraw-Hill 1962 incorporated by reference in its entirety, especially pp. 159 and 168.

Briefly, the usual cation selectivity list in order of decreasing selectivity given by Helfferich is: $Ba^{++}$, $Pb^{++}$, $Sr^{++}$, $Ca^{++}$, $Ni^{++}$, $Cd^{++}$, $Cu^{++}$, $Co^{++}$, $Zn^{++}$, $Mg^{++}$, $UO2^{++}$, $Tl^{+}$, $Ag^{+}$, $Cs^{+}$, $Rb^{+}$, $K^{+}$, $NH4^{+}$, $Na^{+}$, $Li^{+}$.

A usual anion decreasing selectivity list for general purpose anion exchange materials given by Helfferich is: citrate, sulfate, oxalate, iodide, nitrate, chromate, bromide, thiocyanate, chloride, formate, acetate, fluoride.

These lists can be used as starting points for designing separation processes according to the present invention because the selectivity usually (but not always) varies predictably with temperature. Generally, the selectivity of an ion-exchange material decreases with increasing temperature, although there are some exceptions. Thus, an ion (or set of ions) that is strongly held by the adsorbent compared to another ion (or set of ions) at one temperature is even more strongly held at a lower temperature. The ion(s) more strongly held at a lower temperature is (are) hot-released ion(s). Conversely, the ion(s) less strongly held at a lower temperature is (are) cold-released ion(s).

Since some ions may have unusual variations in selectivity with variations in temperature, a moderate amount of routine experimentation may be necessary before a separation process according to the present invention can be implemented.

It is desirable that the temperature difference between hot and cold cycles be as great as practical because the shift in the temperature-dependent selectivity for a given ion (or set of ions) is roughly proportional to the shift in reciprocal absolute temperature. From this point of view, ion exchange materials that can withstand high temperatures are preferred.

Another practical limit to the high temperature is the boiling point of the fluid (the cost of raising the fluid or bed temperature is also a significant factor in design choices). Thus, a typical operating temperature range for the hot cycle is in the range of about 80° C. to about 150° C., preferably about 90° C. to about 110° C. For aqueous solutions of moderate salt concentration, boiling points at ambient pressure will be higher than 100° C. and up to about 120° C. The operating pressure of the process may be increased to keep the solutions from boiling. It is preferred that the pressure be kept higher than about 10 kPa above the vapor pressure of the solvent (e.g. water) at the hot operating temperature and also higher than 100 kPa. An operating pressure above about 480 kPa would suppress boiling of even dilute aqueous solutions to above about 150° C. The upper limit of pressure is not dictated by the process but by equipment and cost considerations.

A third practical limit to the high temperature may be the point of decomposition of the desirable ions. If this is an issue, the hot operating temperature range may be adjusted downwards, as would be known to those skilled in the art.

Practical limits to the cold operating temperature are imposed by freezing of the solution, and refrigeration cost considerations. Also, the rate of transfer between the fluid phase and the ion-exchange material will slow down considerably when the temperature is very low. It is thus preferred that the cold operating temperature be within the range of about −10° C. to about +40° C. with a range of about 0° C. to about +30° C. being particularly preferred.

The stream enriched in the desirable ion will provide a gross product. Part of the gross product is sent back to another bed or train as a reflux; the rest is taken as net product. (The stream impoverished in the desirable ion will also provide a gross product, which may be collected or discarded, depending on its value. Part of this stream as well will be used as a reflux.) If the reflux flow of the stream enriched in the desirable ion is made large enough, then the purity of the net product can be made very high. This is because the ion pumping action in each of the beds in each direction cumulatively adds more of the desirable ion(s) (for that direction) and removes more of the undesirable ion(s). The pumping action of the process can effect a separation even when the difference in selectivity between the higher and the lower temperature is not large, as long as enough reflux is used. If the selectivity differs slightly between the higher and lower temperatures, then the forward and backward streams have nearly the same concentrations of ion V; but a modest shift in concentration is adequate to pump ion V from one stream into the other. It is preferred that the selectivity coefficient for an ion be at least about 40% higher at one temperature than at the other.

In the specific case of removal of $Na^{+}$-ions from a $Li^{+}$-brine contaminated by $Na^{+}$, the minimum reflux ratio required for essentially complete removal can be calculated as follows. The K-value (selectivity coefficient) is related to the loadings and ion concentrations in solution by:

$$K_{Li}^{Na} = \frac{L_{Na}[Li^+]}{L_{Li}[Na^+]} \quad (4)$$

where: $L_{Na}$ and $L_{Li}$ are the loadings of sodium and of lithium on the zeolite and $[Na^+]$ and $[Li^+]$ are the respective concentrations in solution.

The "storage" X on the bed is the sum of the loadings plus the amount in the solution stored in the void spaces of the zeolite. For a void zeolite fraction $\epsilon$:

$$X_{Na} = L_{Na} + \epsilon[Na^{30}] \quad (5)$$

$$X_{Li} = L_{Li} + \epsilon[Li^{30}] \quad (6)$$

$$X_T = X_{Na} + X_{Li} = \text{constant} \quad (7)$$

These relations may be used to estimate the mass transfer that is occurring at a particular point on the bed when the temperature is changed. The total storage remains constant on the bed but the loadings and solution concentrations can change. A simple iterative computational procedure can be used to ascertain the new loadings and concentrations that result from a given change in the temperature, based on equations 4 through 7 above as well as diffusion (rate of transfer) considerations given below.

For very dilute solutions the storage is approximately equal to the loading and, furthermore, the loadings change only slightly when the temperature is changed. (This approximation is useful when the concentration mols/m³ of each ion is less than 1% as high in the solution as on the ion-exchange material.) Applying this approximation to Equations (3) and (4), one obtains:

$$\left(\frac{[Na^+]}{[Li^+]}\right)_{370} = \frac{(K_{Li}^{Na})_{298}}{(K_{Li}^{Na})_{370}} \left(\frac{[Na^+]}{[Li^+]}\right)_{298} \quad (8)$$

$$= \frac{9.77}{5.43} \left(\frac{[Na^+]}{[Li^+]}\right)_{298}$$

$$= 1.8 \left(\frac{[Na^+]}{[Li^+]}\right)_{298}$$

The factor 1.8 in Equation (8) is the calculated shift in the ratio of sodium concentration to lithium concentration caused by the shift in temperature. The concentration shift is the "cycle selectivity" for a pair of ions, in this case lithium over sodium in the cold-released product. The same factor will be the cycle selectivity for sodium over lithium in the hot-released product. Thus, cycle selectivity of one ion over another is a function of the flow (stream) in which, and the temperature at which the one ion is selectively released. This is illustrated in the calculations in Equation (8).

Increasing the temperature from 298 K to 370 K nearly doubles the $Na^+$ concentration in the solution. An iterative computational procedure would yield more precise values of the concentration changes and would not depend on the dilute-solution approximation.

In order to remove all of the $Na^+$ from a forward flowing $Li^+$-brine, the $Na^+$ enriched reflux stream must have a higher $Na^+$ concentration. A mass balance on the $Na^+$ (around beds B and D in FIG. 1) determines the minimum reflux required. Under the approximation used to obtain Equation (8), the $Na^+$-rich maximum reflux flow is found to be some 60% of the forward flow.

C. Duplex Ion-Exchange Process

As shown in FIG. 1, two beds, A and B, can be attached in series (in a train) to form a duplex unit. The unit is "duplex" in that the feed point is intermediate to the two beds, such that both the forward flow will be enriched in content of the ion (or set of ions) as it moves towards its exit, and the backward flow will be enriched in content of another ion (or set of ions) as it moves from the feed point towards the backward flow exit. The advantage of a duplex unit is that lithium (for example) can be nearly 100% recovered and at nearly 100% purity. A second duplex unit, C and D, is included to show the operation of the entire thermal-swing process. In FIG. 1, during the first phase, beds A and B are the hot zone and beds C and D are the cold zone, but the means of controlling the temperature is not shown in FIG. 1 for simplicity.

In general, there are two ways to make a "temperature-swing" process. One way is to heat or cool the ion-exchange beds. There are well-known means for heating and cooling the beds, such as with imbedded coils and/or external jackets, heated by steam or electrically. Cooling can be achieved with cooling water or with standard refrigeration fluids and techniques. An example of an ion-exchange bed 301 with internal coils 302, for heating or cooling, is depicted schematically in FIG. 3.

Figure 4:
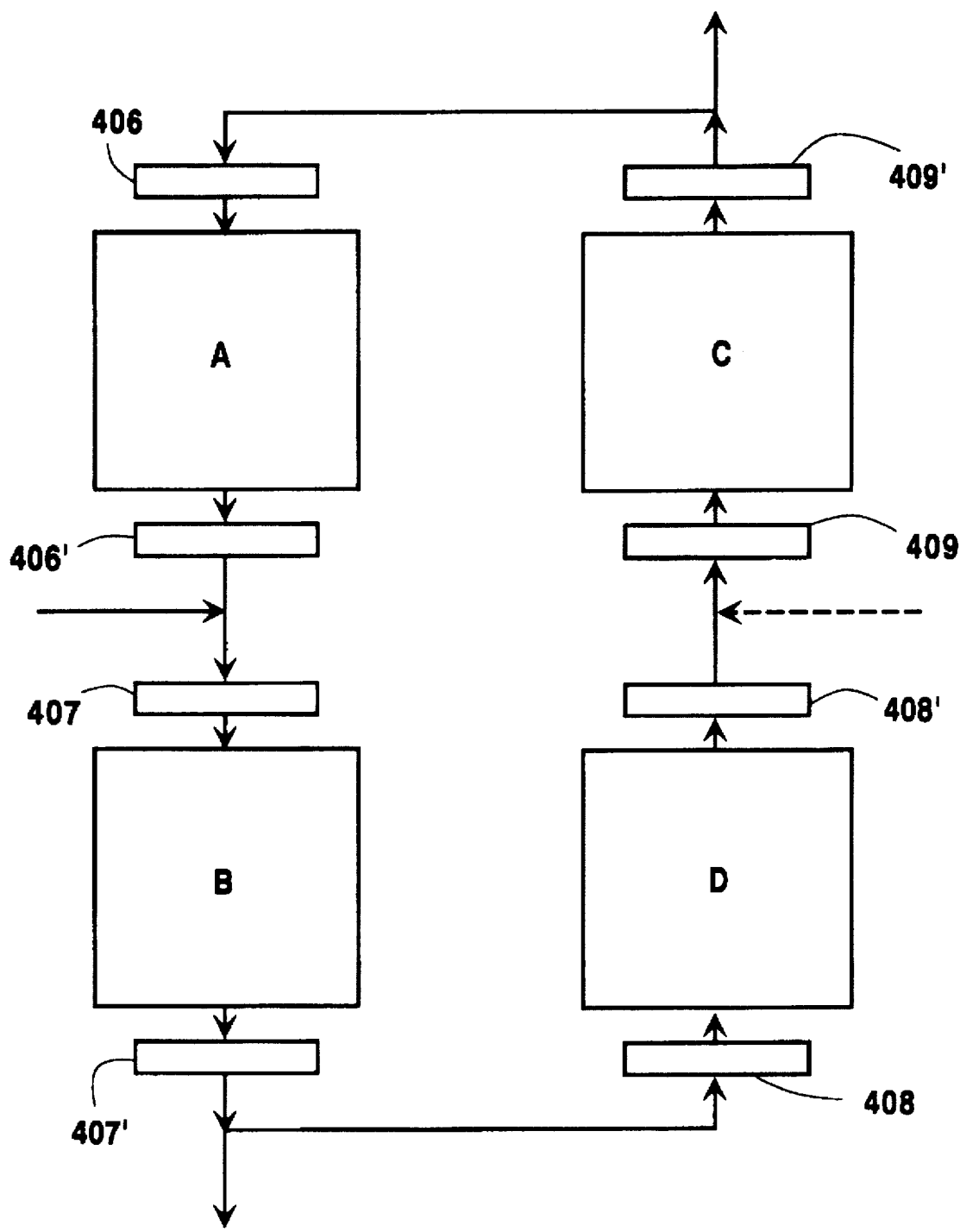
FIG. 4 is a process schematic of a duplex lithium separation (recovery) process according to the invention employing two trains of two beds each and depicting an alternative method for temperature control using heating and cooling of fluids, instead of heating and cooling of ion-exchange beds.

An alternative means of controlling the temperature is to heat and/or cool the ion solutions entering the beds. Such a process is shown schematically in FIG. 4. The brines flowing downward into beds A and B are heated in heater 406 (for the reflux) and in heater 407 for the feed prior to entering the beds during the hot phase in beds A & B. Similarly, the fluids flowing upward into beds D and C are cooled in cooler 408 for the reflux and 409 for the feed if fed on the "cold" phase for beds C and D. The products that are refluxed can be also passed through heat exchangers (not shown) to recover the sensible heat in the fluid streams before heating or cooling, respectively. The unlabeled blocks 406'–409' depict coolers (406', 407') or heaters (408', 409') used when the hot and cold zones are switched, when heaters 406, 407 and coolers 408, 409 are not used.

Either or both means for controlling temperature and effecting the "temperature-swing" are within the scope of the invention.

Figure 3:
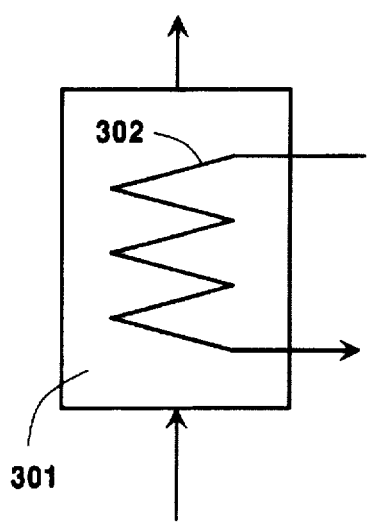
FIG. 3 is a schematic of one type of temperature control means (cooling or heating) with heat-exchange coils embedded in the ion-exchange bed that can be employed in the process of the invention.
Figure 5:
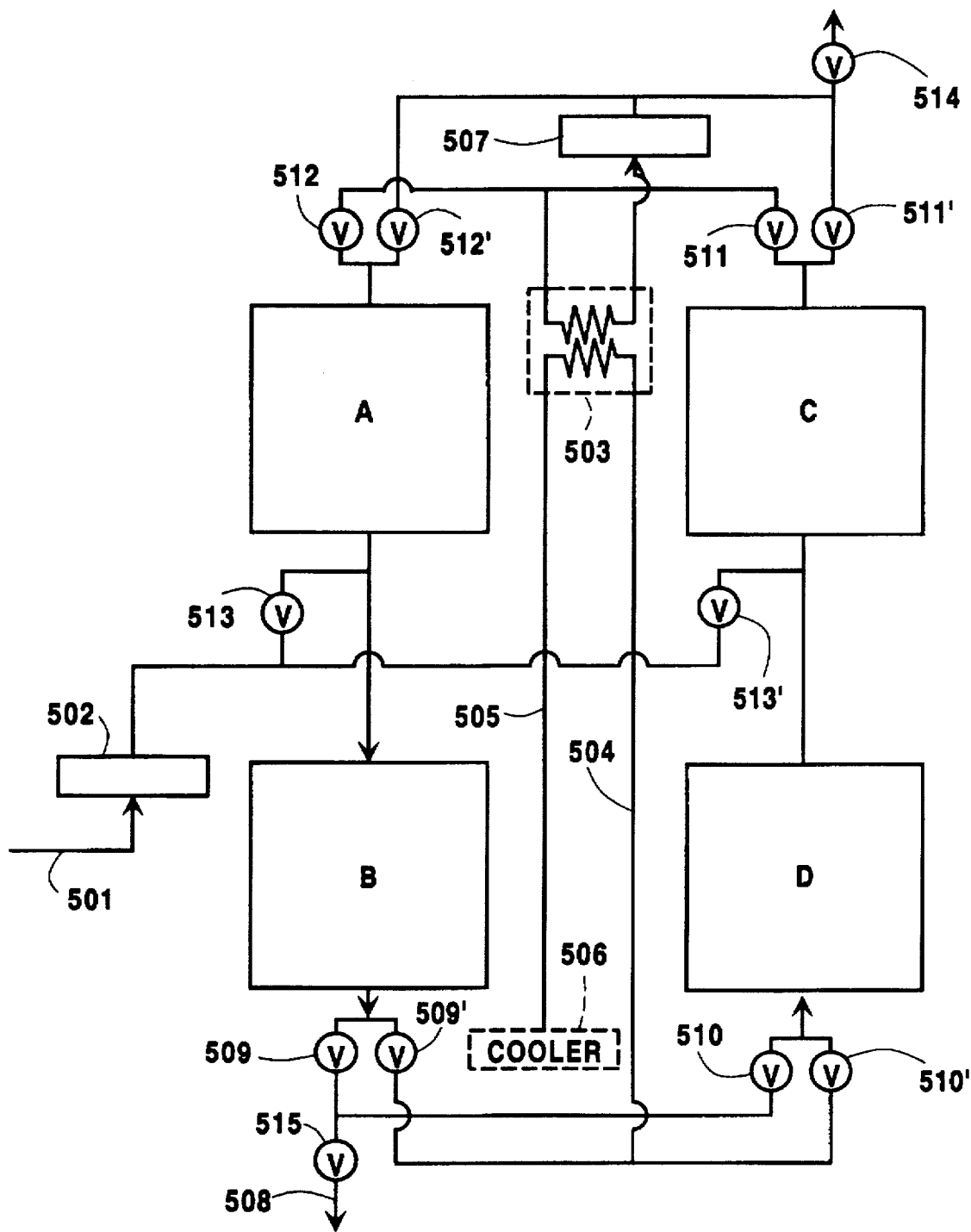
FIG. 5 is a process schematic of a preferred duplex embodiment of the invention utilizing fluid heating and cooling and illustrating a heat-exchange option.

A more complete process diagram (including temperature control) for a representative *Duplex, Temperature-Swing, Ion-Exchange Process* is shown in FIG. 5. In the process shown, the feed brine 501 is chilled in (cooling) element 502 before entering the cold-zone beds (C and D during the first phase) or (heating) element 502 warms the brine before it enters the warm-zone beds (A and B during the first phase). A heat exchanger HX 503, is employed to exchange the heat from the reflux streams 504 and 505 passing between the warm and cold zones. If needed, an additional cooler 506 and heater 507 can be added as shown by the boxes in the dashed lines. If necessary or desirable, another heat exchanger (not shown) could be added to recover refrigeration from the $Na^+$-rich product stream 508 to help cool the feed stream 501. Furthermore, it may be desirable to heat and cool the beds instead of (or in addition to) the brine streams with external heat-exchange fluids, by the use of heat-exchange means, e.g., heating jackets or embedded coils as shown in FIG. 3. Temperature control is provided by conventional temperature control means.

If the beds themselves are heated (cooled), rather than the process fluids, the high and low temperatures can be established quickly before the ion-exchange is performed. This is advantageous because it decreases the time it takes the temperature to reach the proper level for each side but it may require suspension of the brine flows while the temperature is being changed. Also, the beds themselves must supply all the heat or refrigeration to change the temperature of the brines, which is costly. Conversely, when the process brines are heated (cooled), these fluids alone must supply the energy needed to alter the bed temperatures. In this case, a temperature "wave" is established that precedes the ion-exchange "wave" through the bed. The principal disadvantage of this procedure is that, for part of the time, the "temperature-swing" is attenuated with a resulting decrease in efficiency. The preferred mode of operation would be to heat (cool) both the brines and the beds, if this is economically feasible, but either of the aforedescribed methods can be used in practice.

The process of the invention is a cyclic process. When unwanted ions "break through" into a product stream, i.e. when specifications for that product stream are exceeded, the flows through the beds must be reversed, and the temperatures of the beds (or trains) must be changed. Each flow path in FIG. 5 is provided with the necessary pumps (preferably bi-directional) and valves or other conventional flow control means. For simplicity, examples of pumps are shown in FIG. 1.

The simplest process applicable to the equipment shown in FIG. 5, is a two-step process given in the following table:

TABLE 2

Two-Step Temperature-Swing Process Cycle
For FIG. 5 Process

| | Beds A & B | | Beds C & D | |
|---|---|---|---|---|
| Step | Flow | Temperature | Flow | Temperature |
| 1 | Upward | Cooling or Cold | Downward | Heating or Hot |
| 2 | Downward | Heating or Hot | Upward | Cooling or Cold |

These conditions can be achieved by appropriate switching of the valves 509–513 and 509'–513' in FIG. 5. Products are collected through valves 514 and 515, respectively.

The disadvantage of the two-step cycle is that the bed temperatures are inverted from the desired temperatures at the start of each step. The heating and cooling must all be accomplished by the flowing brine streams, or by external means while the brine is flowing. This difficulty can be alleviated by employing a four-step process as shown in Table 3.

TABLE 3

Four-Step Temperature-Swing Process Cycle

| | Beds A & B | | Beds C & D | |
|---|---|---|---|---|
| Step | Flow | Temperature | Flow | Temperature |
| 1 | Upward | Cold | Downward | Hot |
| 2 | Off | Heating | Off | Cooling |
| 3 | Downward | Hot | Upward | Cold |
| 4 | Off | Cooling | Off | Heating |

In this four-step cycle external heating of the beds must be used, since the brine flow is suspended during steps 2 and 4. Imbedded coils, as shown in FIG. 3, could be activated during these steps.

D. Simplex Process for Lithium Recovery

The duplex process consists of two halves, each containing two ion-exchange beds. The top half (with reference e.g. to FIGS. 1 or 4) is a purification section that acts to remove from the fluid phase the "impurity" (undesirable) ion(s), that in this example have the higher absorbency on the ion-exchange materials at lower temperatures, from the "product" (desirable) ion(s), that in this example have the higher absorbency at higher temperatures. The bottom half (again with reference e.g. to FIGS. 1 or 4) is a recovery section that keeps the top "product" ions in the system and out of the bottom discharge stream. The methods described above can be used to determine the bottom reflux ratio required for a specified "recovery", i.e. content of lithium/unit product divided by content of lithium/unit feed.

Figure 7:
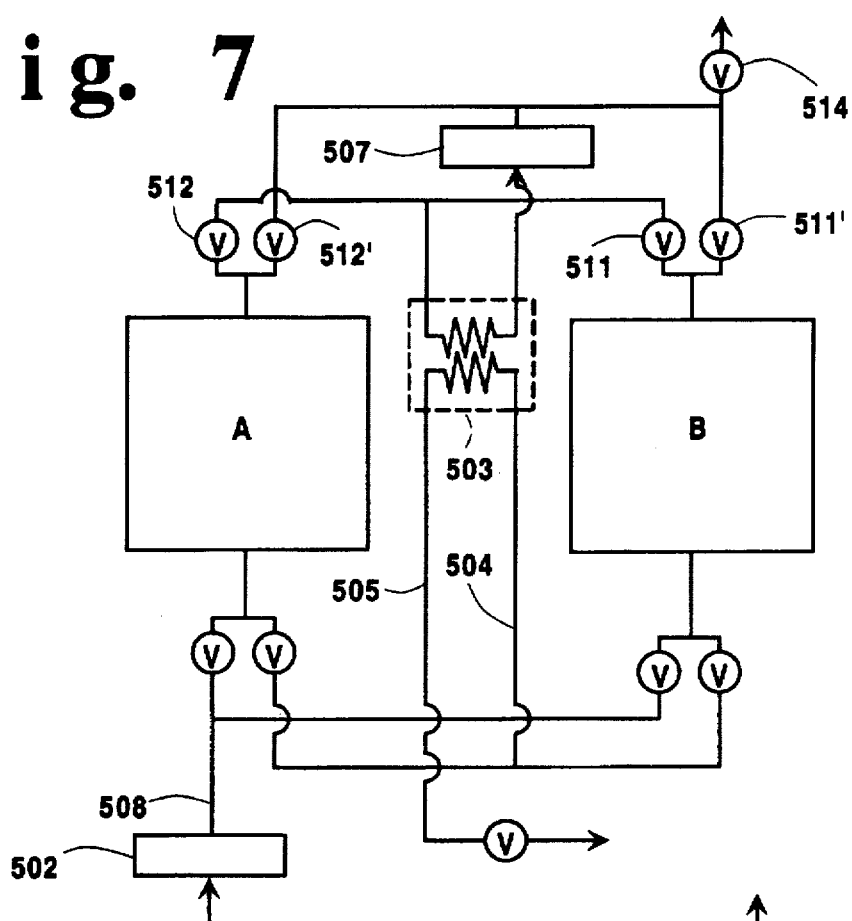
FIG. 7 is a process schematic of a simplex two-bed separation process (two trains of one bed each) according to the present invention which is preferred when an ion (e.g $Li^+$) is removed from relatively low-ion-value brines that may be relatively dilute.

If loss of lithium is not important, the top half alone could suffice to purify the product, provided the amount of reflux, as determined in section (B) is sufficient. (An example of such a two-bed purification process is shown in FIG. 7.) Where lithium loss must be kept small, the full duplex process should be used. In addition, external lithium may be added to the system (or to a product) to adjust lithium content of the product to fit a specification.

Figure 8:
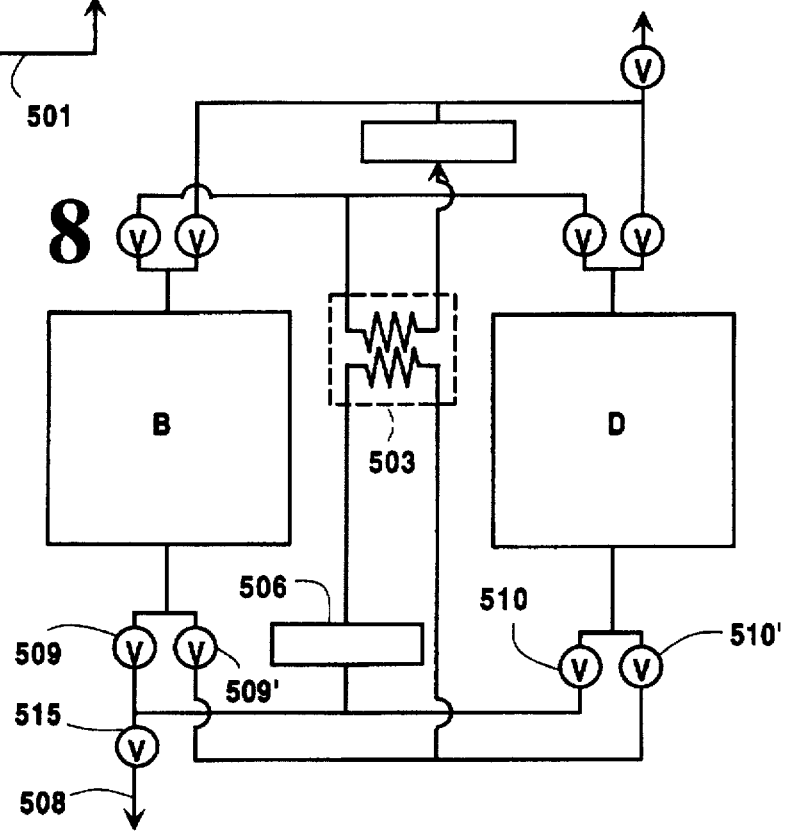
FIG. 8 is a process schematic of an inverted simplex, two-bed separation process (two trains of one bed each) according to the invention in which trace quantities of lithium are removed from brines of other ions. The FIG. 8 process is inverted in that the product stream ($Li^+$-impoverished brine) is collected off the cold bed.

If lithium product purity is not important, the bottom half alone can be used as in FIG. 8.

Example of Duplex Process for Lithium Recovery

Figure 6:
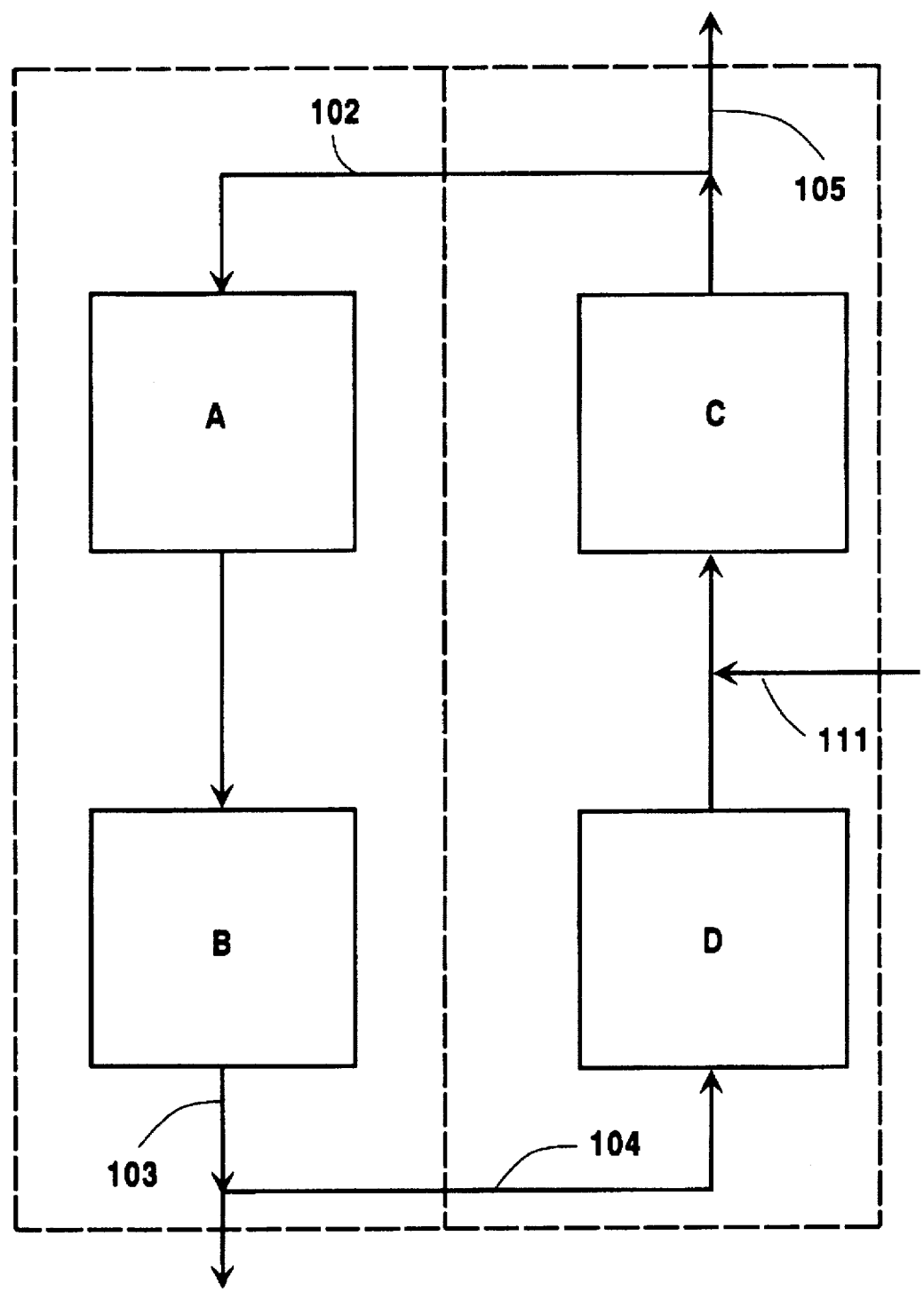
FIG. 6 is a process schematic of a particular duplex embodiment according to the invention.

The data in Table 1 have been used to estimate the relative flows applicable to a duplex ion-exchange process, operating between 298 and 370 K, for 97% recovery of $Li^+$ from a brine that has ⅞ $Li^+$-ions and ⅛ $Na^+$-ions and a total ion storage of the order of 1000 mol/m$^3$ of brine. The relative flows for the process streams for the first phase are shown in FIG. 6, otherwise identical to FIG. 1, with the feed being introduced at 111. The purity of the top-end $Li^+$-product is specified at 99.8%. For the specified recovery, the bottom (discharge) Na-enriched brine is 82.4 equivalent % $Na^+$ and 17.6% $Li^+$. In this example, the top-end reflux/product ratio is 2.38, corresponding to a reflux of 70% of the forward flow. On the bottom, the reflux/waste ratio is 12.50, corresponding to a reflux of 92.6% of the backward flow.

To increase the lithium recovery without decreasing the lithium purity, we could increase the reflux flows, increase the bed sizes, and/or increase the surface area of the ion-exchange material. The lithium-enriched product flow would then be increased to accommodate the increased recovery. For example, if the recovery were increased from 97% to 99.9%, the lithium-enriched product flow would have to be increased by the ratio of 99.9/97 or about 1.030.

If part of the sodium ions in the above example were replaced by potassium ions or by potassium, rubidium, and/or cesium ions, then the same flows given in the foregoing example would be used with somewhat better results, since the lithium ions will have greater cycle selectivities over the potassium, rubidium, and cesium ions than over the sodium ions.

If calcium and/or strontium ions were present in addition to the other ions for these examples, they would tend to be distributed between the two products. The reason is that the lithium would have cycle selectivities over them but the cycle selectivities would be less than the cycle selectivity over sodium. The presence of these alkaline earth ions would not directly interfere with the separation of the lithium from the higher alkali metal ions.

If magnesium ions were present, they would tend to go with the lithium ions into the forward product. If much magnesium is present in the feed brine, then the forward product rate should be increased just enough to accommodate magnesium separation.

The example shows that a duplex temperature-swing, ion-exchange process can be constructed according to this invention, using known zeolite ion-exchange materials, that can be used to recover essentially all of the lithium from a mixed lithium-sodium brine and produce a high-purity lithium brine. Such a process would be very useful in the manufacture of specialty lithium-containing zeolites to be used as adsorbents in gas separation.

The process of the invention was developed to recover valuable $Li^+$ ions, primarily from the process streams from the manufacture of special zeolite adsorbents. In this situation, it is important that the losses of $Li^+$ be minimized and the duplex process is preferred. During the cold phase, the function of beds A and B is to retain the $Li^+$ in the system, rather than allowing it to be discharged in the $Na^+$-rich waste stream.

The invention could also be used in other situations where $Li^+$ could be recovered. The invention could be used to recover lithium ions from seawater (the lithium-deprived seawater is discarded). The dilute brines might contain total cation concentrations of 500 to below 0.1 equivalents per cubic meter of solution. Where dilute low-value $Li^+$-rich brines are available, the duplex process is not required to recover most of the lithium. In such cases, a simpler process, here called a "simplex" process, can be used. Such a process is shown schematically in FIG. 7. It is apparent that this process just uses the top half of the duplex process of FIG. 5. The operation of the simplex process is similar to the duplex process. The principal difference is that the waste brine still can contain some $Li^+$ ions, along with $Na^+$ and other ions, but of such low concentration that it is not worthwhile to recover this lithium.

There are other situations where it is required to remove trace quantities of $Li^+$ from brines of other ions (i.e. the lithium product purity is not important). This can be accomplished with an "inverted simplex" process, such as that shown in FIG. 8. This process corresponds to the bottom half of the duplex process of FIG. 5.

A process according to the invention can even be carried out using a single zone as in FIG. 9 (considering FIG. 9 to be an entire process, not a part of a larger system). The zone is first brought to a first operating temperature and the process is carried out using an extraneous solution enriched in desirable ion in lieu of reflux through 102. Part of the bottom product is stored in tank 903 to serve as the "reflux" during the phase at the second temperature. Once specifications for the bottom product are exceeded, the reflux brine 102 is stopped (brine may be stored in tank 902) and the bed is brought into the second operating temperature. During this second phase, reflux 104 is used from tank 903 and part of the top product 105 is stored for future reflux in tank 902. The second phase is terminated when specifications for the top product are exceeded; the reflux brine 104 is stopped (brine may be stored in tank 903 and the bed is again brought to the first operating temperature. The first phase is then repeated, followed by the second phase for as many cycles as desired. The feed 101 in FIG. 9 is shown to be intermediate into the bed, which makes this a duplex-type process (with one train). If purity of the bottom product is not important, the feed could have been at the bottom (101'); or if purity of the top product is not important, the feed could have been at the top (101") of the bed. The feed could be introduced continuously or intermittently during at least a portion of one or both of the hot or cold phase. This is a choice made by the operator of the process based on product specifications and other product control parameters as is well-appreciated in the field of the invention.

The process of this invention is useful to recover lithium in the manufacture of specialty ion-exchanged zeolite adsorbents where lithium is used as an exchange ion. The process could also be used in other commercial operations where $Li^+$ ions are to be recovered or removed from brines containing alkali or alkaline earth salts.

As another non-limiting example, the invention could be used to separate rubidium and cesium from sodium since they have large negative heats of exchange relative to sodium. Since the heats of exchange are negative, the process will discharge a brine stream rich in rubidium and cesium where the same process would discharge a brine stream rich in sodium when used for the lithium-sodium separation.

The invention could also be adapted to separate a mixture of strontium and barium (and if applicable radium) from calcium.

The invention has been described above by reference to specific embodiments. However, many modifications, deletions and omissions are possible as will be apparent to those skilled in the art all within the spirit of the invention and within the scope of the following claims:

What is claimed is:

1. A process for producing a solution enriched in at least one desirable ion (DI) from a feed solution containing DI and at least one undesirable ion (UI), the process comprising in a first phase of a cycle the steps of:

(i) at a first temperature, flowing a solution comprising a reflux portion of a product enriched in said DI through a first zone comprising at least one bed of an ion-exchange material having a higher temperature-dependent selectivity for DI at said first temperature compared to at a second temperature different from said first temperature, and obtaining as the effluent from said first zone a product impoverished in said DI;

(ii) at said second temperature, flowing a solution comprising a reflux portion of said DI-impoverished product from step (i) through a second zone comprising at least one bed of an ion-exchange material having a lower temperature-dependent selectivity for DI at said second temperature compared to at said first temperature, and obtaining as the effluent from said second zone said product enriched in said DI, wherein said DI includes lithium ion, said UI comprises at least one other alkali metal ion, and said ion exchange material comprises zeolite X.

2. The process of claim 1 wherein said ions are cations and the ion-exchange material in said first zone is a cation exchange material, and is the same as the ion-exchange material in said second zone.

3. The process of claim 1 wherein said DI further comprises at least one of calcium and magnesium and said UI further comprises at least one other alkaline earth cation.

4. The process of claim 1, wherein said at least one UI further comprises at least one alkaline earth ion.

5. The process of claim 1 further comprising the step:

(iii) continuing said steps (i) and (ii) until at least one of the DI-enriched and DI-impoverished products contains an amount of DI that does not meet at least one of predetermined purity and recovery specifications for said DI, thereby completing said first phase of a cycle.

6. The process of claim 5 further comprising in a second phase of a cycle the steps of:

(iv) flowing a solution comprising a reflux portion of the product impoverished in said DI through said first zone at a third temperature substantially equal to said second temperature, and obtaining a DI-enriched product as the effluent from said first zone; and (v) flowing a solution comprising a reflux portion of said DI-enriched product from step (iv) through said second zone at a fourth temperature substantially equal to said first temperature and obtaining as the effluent from said second zone the DI-impoverished product referred to in step (iv); wherein the flow pattern created by steps (iv) and (v) during said second phase is reversed compared to the flow pattern created by steps (i) and (ii) during said first phase of a cycle.

7. The process of claim 6 wherein at least one of the solutions flown into said second zone in step (ii) and into said second zone in step (ii) and (v) further comprises the feed solution.

8. The process of claim 6 further comprising the step:

(vi) continuing said steps (iv) and (v) until at least one of the DI-enriched and DI-impoverished products contains an amount of DI that does not meet at least one of predetermined purity and recovery specifications, thereby completing said second phase of a cycle.

9. The process of claim 8, further comprising adding one or more cycles to said process by alternatively repeating said first phase of the cycle and said second phase of the cycle.

10. The process of claim 8 wherein said feed solution is flown into said first zone during steps (i) through (iii) and into said second zone during steps (v) through (vi).

11. The process of claim 8 wherein said first zone and said second zone each comprise at least two in-series beds of ion exchange material and wherein said feed solution is fed between the first and second bed of the first or second zone and caused to join the flow pattern created by steps (i) through (iii) or the flow pattern created by steps (iv) through (vi), respectively.

12. The process of claim 8 wherein at least one of the solutions flown into said first zone in step (i) and in step (iv) further comprises the feed solution and each of said zones comprises one bed of ion-exchange material.

13. The process of claim 8, wherein said feed solution is flown into the zone during at least a portion of at least one of step (i) and step (ii).

14. A process for producing a solution enriched in at least one desirable ion (DI) from a feed solution containing DI and at least one undesirable ion (UI), the process comprising in a first phase of a cycle the steps of:

(i) at a first temperature, flowing a solution comprising a reflux portion of a product enriched in said DI through a first zone comprising at least one bed of an ion-exchange material having a higher temperature-dependent selectivity for DI at said first temperature compared to at a second temperature different from said first temperature, and obtaining as the effluent from said first zone a product impoverished in said DI;

(ii) at said second temperature, flowing a solution comprising a reflux portion of said DI-impoverished product from step (i) through a second zone comprising at least one bed of an ion-exchange material having a lower temperature-dependent selectivity for DI at said second temperature compared to at said first temperature, and obtaining as the effluent from said second zone said product enriched in said DI, wherein said DI comprises lithium ion, said UI comprises at least one other alkali metal ion, and said ion-exchange material comprises zeolite X.

15. The process of claim 14 wherein said DI further comprises at least one of calcium and magnesium and said UI further comprises at least one other alkaline earth cation.

16. A process for producing a solution enriched in at least one desirable ion (DI) from a feed solution containing DI and at least one undesirable ion (UI), the process comprising the steps of:

(i) feeding said solution in a first direction into a zone at a first temperature, said zone comprising at least one bed of ion exchange material having a higher temperature-dependent selectivity for DI at said first temperature than at a second temperature different from said first temperature and obtaining as the effluent from said zone a product impoverished in said DI;

(ii) stopping said step (i) and changing the temperature of said zone to said second temperature;

(iii) flowing into said zone at said second temperature and in a second direction opposite to the first direction the feed solution and a reflux comprising a portion of said DI-enriched product obtained in step (i) and obtaining a solution enriched in said DI;

(iv) stopping said step (iii) and changing the temperature of said zone to said first temperature; and (v) repeating steps (i) through (iv), wherein said DI includes lithium ion, said UI comprises at least one other alkali metal ion, and said ion exchange material comprises zeolite X.

17. A process for producing a solution enriched in at least one desirable ion (DI) from a feed solution containing DI and at least one undesirable ion (UI), the process comprising the steps of:

(i) at a first temperature, flowing a solution comprising a reflux portion of a product enriched in said DI through a zone in a first flow direction, said zone comprising at least one bed of an ion-exchange material having a higher temperature-dependent selectivity for DI at said first temperature compared to at a second temperature different from said first temperature, and obtaining as the effluent from said zone a product impoverished in said DI;

(ii) at said second temperature, flowing a solution comprising a reflux portion of said DI-impoverished product from step (i) through the zone in a second flow direction counterflow to said first direction, and obtaining as the effluent from said zone said product enriched in said DI;

(iii) alternating said steps (i) and (ii) until at least one of the DI-enriched and DI-impoverished products contains an amount of DI or UI that meets at least one of predetermined purity and recovery specifications for said ion, wherein said DI includes lithium ion, said UI comprises at least one other alkali metal ion, and said ion-exchange material comprises zeolite X.

* * * * *